US006761686B2

(12) United States Patent
Takase (10) Patent No.: US 6,761,686 B2
(45) Date of Patent: Jul. 13, 2004

(54) ENDOSCOPE

(75) Inventor: Seisuke Takase, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 09/902,405

(22) Filed: Jul. 10, 2001

(65) Prior Publication Data

US 2002/0019582 A1 Feb. 14, 2002

(30) Foreign Application Priority Data

Jul. 12, 2000 (JP) .......................................... 2000-211575

(51) Int. Cl.$^7$ .......................................... A61B 1/005
(52) U.S. Cl. ........................................ 600/140; 600/133
(58) Field of Search ................................ 600/133, 139, 600/140, 144, 130

(56) References Cited

U.S. PATENT DOCUMENTS

| | | | | |
|---|---|---|---|---|
| 4,753,222 A | * | 6/1988 | Morishita | 600/140 |
| 4,944,287 A | * | 7/1990 | Takahashi et al. | 420/401 |
| 5,217,002 A | * | 6/1993 | Katsurada et al. | 600/139 |
| 5,235,964 A | * | 8/1993 | Abenaim | 600/139 |
| 5,448,988 A | * | 9/1995 | Watanabe | 138/118 |
| 5,685,825 A | * | 11/1997 | Takase et al. | 528/59 |
| 5,788,714 A | * | 8/1998 | Ouchi | 138/123 |
| 5,885,207 A | * | 3/1999 | Iwasaka | 600/139 |
| 5,924,977 A | * | 7/1999 | Yabe et al. | 600/121 |
| 6,329,069 B1 | * | 12/2001 | Azizi et al. | 428/600 |

FOREIGN PATENT DOCUMENTS

| | | |
|---|---|---|
| JP | 2-283346 | 1/1990 |
| JP | 8-136823 | 5/1996 |
| JP | 11-56762 | 3/1999 |

* cited by examiner

Primary Examiner—John P. Leubecker
(74) Attorney, Agent, or Firm—Scully, Scott, Murphy & Presser

(57) ABSTRACT

An endoscope has an insertion member that includes a flexible tube. The flexible tube has a spiral tube, which is formed by spirally winding a metallic belt, sheathed with a braid, and has the braid sheathed with a resin sheathing. The resin sheathing is made of an ester-series thermoplastic elastomer, an amide-series thermoplastic elastomer, or a blend of them. Therefore, the flexural rigidity of the flexible tube of the insertion member attained at a predetermined position after the flexible tube is loaded during high-temperature high-pressure steam sterilization is equal to or lower than that attained before the flexible tube is loaded. Consequently, the flexural rigidity of the flexible tube attained after sterilization with high-temperature high-pressure steam is equal to or lower than that attained before the sterilization. Thus, the inserting smoothness of the insertion member can be optimized.

21 Claims, 3 Drawing Sheets

ENDOSCOPE

This application claims benefit of Japanese Application No. 2000-211575 filed in Japan on Jul. 12, 2000, the contents of which are incorporated by this reference.

BACKGROUND OF THE INVENTION

1. Field of the Invention

The present invention relates to an endoscope, or more particularly, to an endoscope having an insertion member that includes a flexible tube, and capable of being autoclaved (sterilized with high-temperature high-pressure steam).

2. Description of the Related Art

In the medical field, endoscopes are widely adopted these days. The endoscope has an elongated insertion member thereof inserted into a body cavity in order to observe a deep region in the body cavity, or has, if necessary, a therapeutic accessory passed through it in order to perform a cure or treatment. As for the medical equipment, it is essential to thoroughly disinfect or sterilize the used endoscope.

Recently, autoclaving (high-temperature high-pressure steam sterilization) has come to be a mainstream of sterilization of endoscope equipment. This is attributable to the fact that autoclaving is less labor-intensive, renders the endoscope usable immediately after completion of sterilization, and is less expensive.

Typical regulations for autoclaving are stipulated in the standard ANSI/AAMI ST37-1992 approved by the American National Standards Institute (ANSI) and published from the Association for the Advancement of Medical Instrumentation (AAMI). According to the standard, a pre-vacuum sterilization process should be performed at 132° C. for 4 minutes and a gravity settling sterilization process should be performed at 132° C. for 10 minutes.

The environmental conditions for autoclaving are quite severe for endoscopes. For realizing an endoscope that meets the environmental conditions and that is so durable as to be autoclaved, various measures must be taken against high pressure, high temperature, and steam unlike realization of an endoscope that is reusable only after disinfected or sterilized according to any other means. In particular, an insertion member of the endoscope that is inserted into a patient's body is required to offer various delicate properties including flexibility and resiliency. Because the insertion member tends to be more susceptible to high pressure, high temperature, and steam than a distal rigid part (the properties of the insertion member are likely to be degraded), more sophisticated measures must be taken in relation to the insertion member.

As described, for example, in Japanese Unexamined Patent Application Publication No. 2-283346, a conventional endoscope capable of being autoclaved has an elongated insertion member that includes a flexible tube composed of a spiral tube, a braid, and a sheathing layer. The spiral tube has a metallic belt wound spirally. The spiral tube is sheathed with the braid, and the braid is sheathed with the sheathing layer that is made of a resin.

However, as far as the endoscope described in the Japanese Unexamined Patent Application Publication No. 2-283346 is concerned, when the endoscope is sterilized using an autoclave (a high-temperature high-pressure steam sterilizer), the sheathing of the flexible tube of the insertion member gets harder. This is because the sheathing is thermally loaded during high-temperature high-pressure steam sterilization. The flexural rigidity of the flexible tube, that is, the ratio of force applied to a predetermined length in longitudinal directions of the flexible tube to a magnitude of bend of the length gets higher. Consequently, the whole insertion member is hardened.

Moreover, a user does not expect that the hardness of the flexible tube attained after sterilization with high-temperature high-pressure steam gets higher than it originally is before the sterilization. If the user uses the endoscope in the same manner as he/she does before the flexible tube gets harder, the user may fail to insert the insertion member into the large intestine or the like such as a tortuous intracavitary organ having many bent parts. Otherwise, if the flexural rigidity of the flexible tube gets lower than the original flexural rigidity, there is a fear that maneuverability may somewhat deteriorate. Nevertheless, the insertion member can be advanced smoothly through the large intestine or any other tortuous organ.

SUMMARY OF THE INVENTION

The present invention attempts to break through the current foregoing situation. An object of the present invention is to provide an endoscope having the inserting smoothness of an insertion member thereof optimized. That is to say, the endoscope is designed so that the flexural rigidity of a flexible tube attained after sterilization with high-temperature high-pressure steam will be equal to or lower than the flexural rigidity thereof attained before the sterilization.

According to the first aspect of the present invention, there is provided an endoscope having an insertion member that includes a flexible tube having a spiral tube, which is formed by spirally winding a metallic bent, sheathed with a braid and having the braid sheathed with a sheathing made of a resin.

In the endoscope, the flexural rigidity of the flexible tube of the insertion member attained at a predetermined position at the room temperature after the flexible tube is loaded during high-temperature high-pressure steam sterilization is equal to or lower than the flexural rigidity attained before the flexible tube is loaded.

Owing to the foregoing constituent feature, the flexural rigidity of the flexible tube attained after sterilization with high-temperature high-pressure steam is equal to or lower than the flexural rigidity thereof attained before the sterilization. This results in the endoscope having the inserting smoothness of the insertion member optimized.

According to the second aspect of the present invention, there is provided an endoscope in which the hardness of a resin sheathing of a flexible tube attained at the room temperature after the sheathing is loaded during high-temperature high-pressure steam sterilization is equal to or lower than the hardness thereof attained before the sheathing is loaded.

According to the third aspect of the present invention, there is provided an endoscope in which when a flexible tube contracts in longitudinal directions at the room temperature after loaded during high-temperature high-pressure steam sterilization, even if the flexible tube is held bent by a predetermined magnitude of bend at the room temperature after loaded during high-temperature high-pressure steam sterilization, the adjoining belt portions of a spiral tube of the flexible tube do not come into contact with one another.

According to the fourth aspect of the present invention, there is provided an endoscope capable of being sterilized with high-temperature high-pressure steam at the temperature ranging from substantially 115° C. to substantially 140° C. at a loading step.

According to the fifth aspect of the present invention, there is provided an endoscope in which the resin sheathing of a flexible tube thereof is made of a resin of either an ester-series thermoplastic elastomer or an amide-series thermoplastic elastomer.

DESCRIPTION OF THE PREFERRED EMBODIMENTS

Referring to the drawings, an embodiment of the present invention will be described below.

Figure 1:
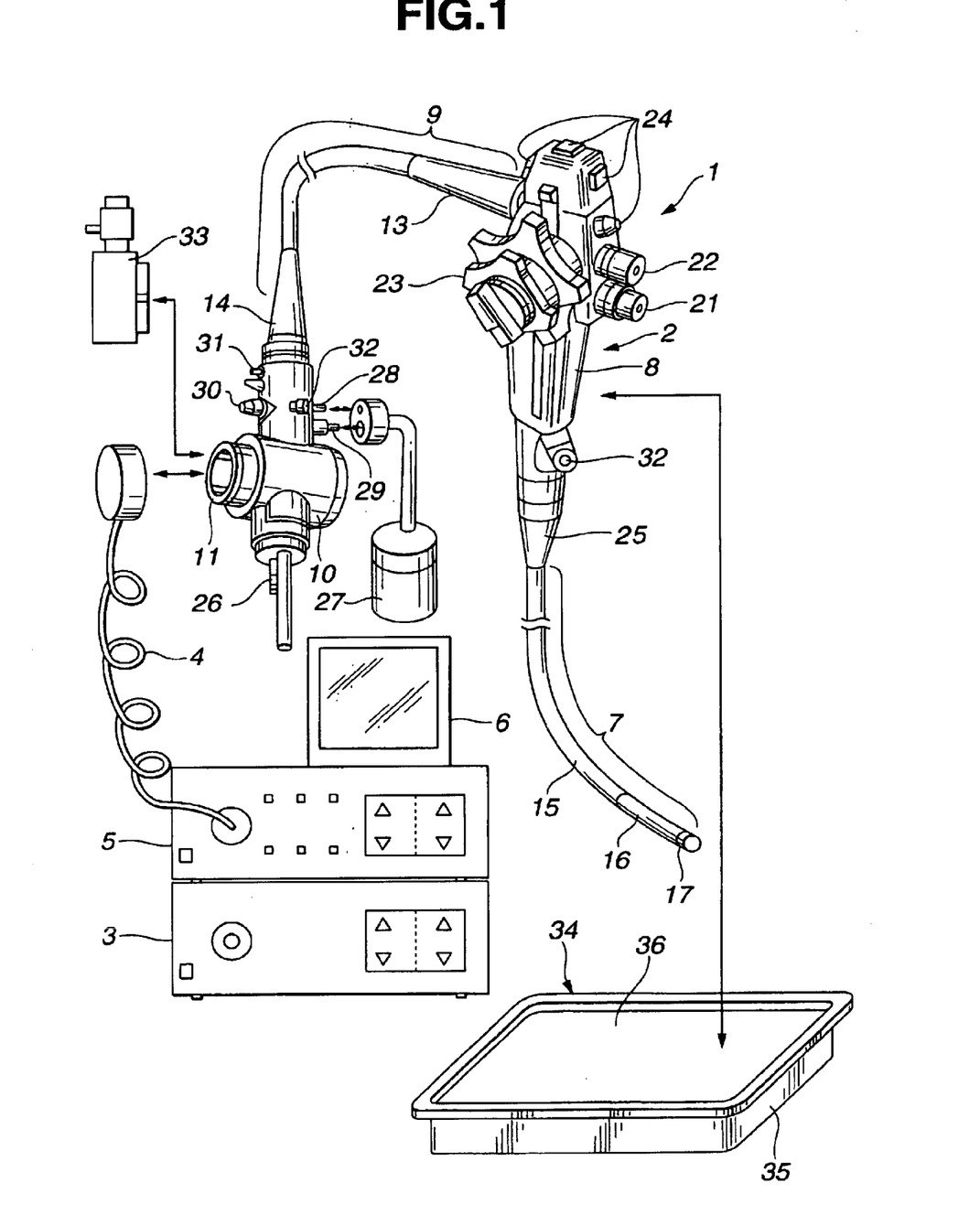
FIG. 1 shows the overall configuration of an endoscope system in accordance with an embodiment of the present invention.
Figure 2:
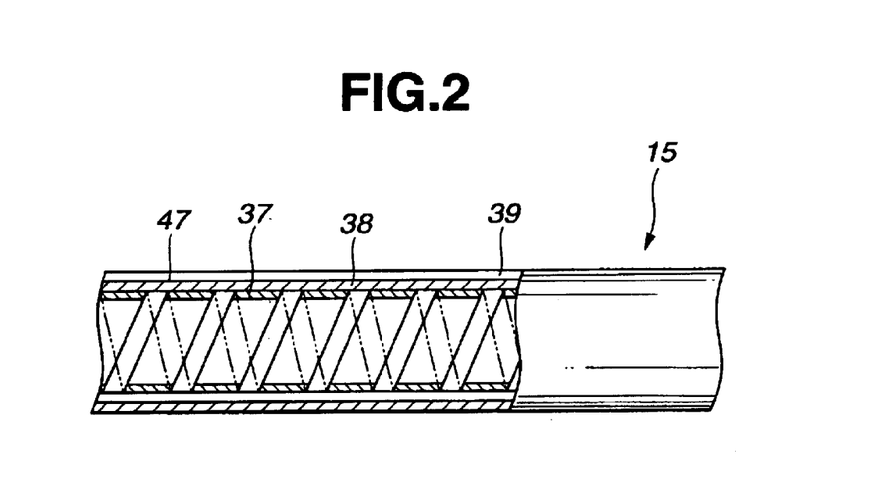
FIG. 2 is a partly sectional view showing a flexible tube of an insertion member of an endoscope shown in FIG. 1.
Figure 3A:
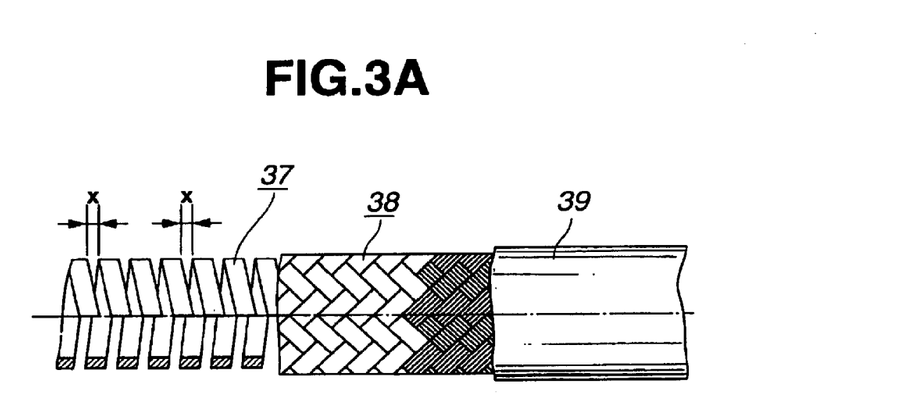
FIG. 3A to FIG. 3E are explanatory diagrams showing in details the structure of the flexible tube shown in FIG. 2.
Figure 3B:
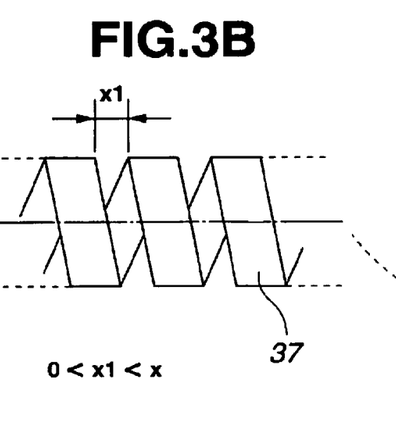
Figure 3C:
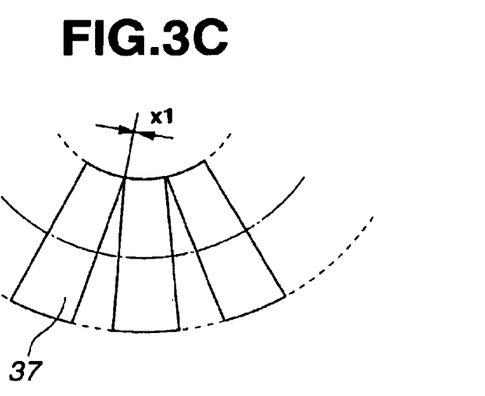
Figure 3D:
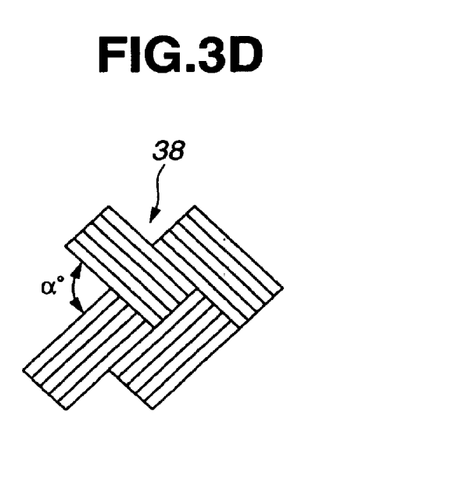
Figure 3E:
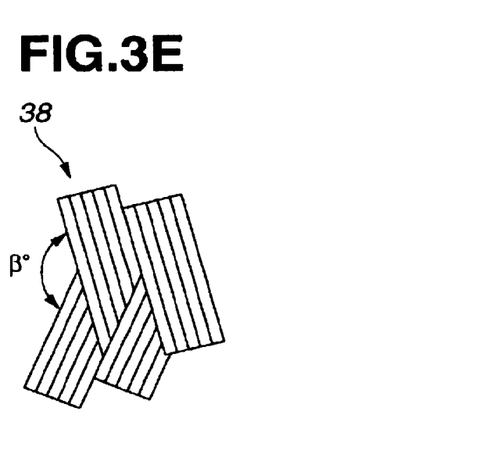
Figure 4:
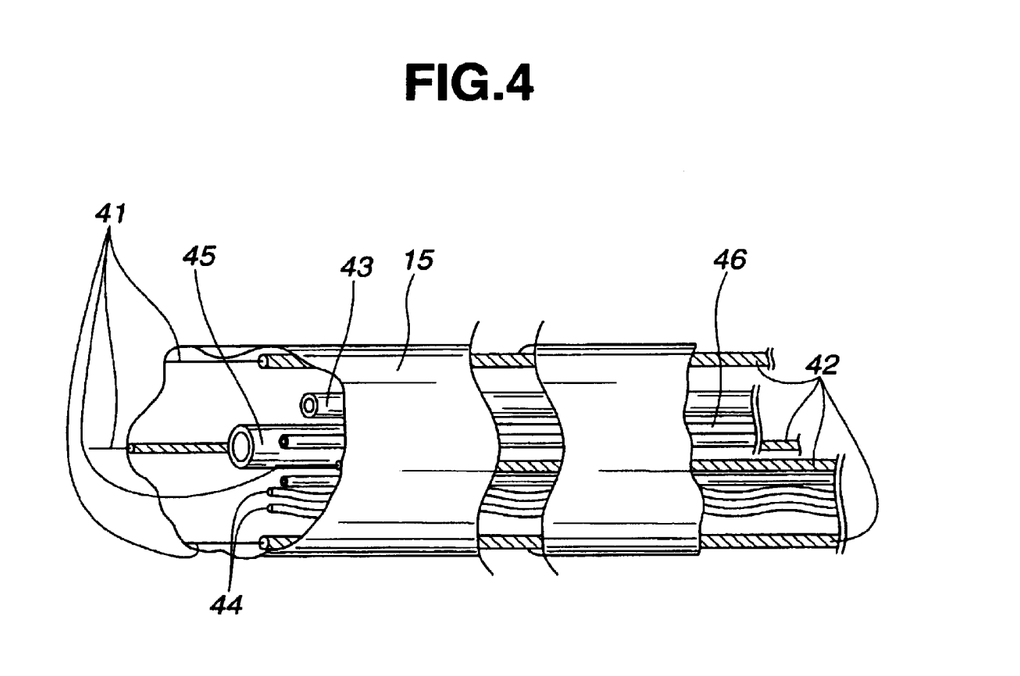
FIG. 4 is an explanatory diagram showing built-in components passed through the flexible tube shown in FIG. 2.

FIG. 1 to FIG. 4 are concerned with the embodiment of the present invention. FIG. 1 shows the overall configuration of an endoscope system employing the embodiment of the present invention. FIG. 2 is a partly sectional view showing a flexible tube of an insertion member of an endoscope shown in FIG. 1. FIG. 3A is an explanatory diagram showing the members of the flexible tube to thus show in details the structure of the flexible tube shown in FIG. 2. FIG. 3B is an explanatory diagram showing a spiral tube shown in FIG. 3A. FIG. 3C is an explanatory diagram showing the spiral tube with the flexible tube shown in FIG. 3B bent. FIG. 3D is an explanatory diagram showing a braid shown in FIG. 3A. FIG. 3E is an explanatory diagram showing the braid with the flexible tube shown in FIG. 3D bent. FIG. 4 is an explanatory diagram showing built-in components passed through the flexible tube shown in FIG. 2.

As shown in FIG. 1, an endoscope system 1 having the embodiment of the present invention consists mainly of an endoscope 2, a light source apparatus 3, a video processor 5, and a monitor 6. The endoscope 2 has an imaging means that is not shown. The light source apparatus 3 is attached to the endoscope 2 so that it can be detached freely, and supplies illumination light to a light guide lying through the endoscope 2. The video processor 5 connected to the endoscope 2 over a signal cable 4 controls the imaging means incorporated in the endoscope 2, and processes a signal produced by the imaging means so as to produce a standard video signal. The video signal produced by the video processor 5 is transferred to the monitor 6, and an endoscopic image is displayed on the monitor 6. After used for observation or treatment, the endoscope 2 is cleaned and autoclaved (sterilized with high-temperature high-pressure steam).

The endoscope 2 consists mainly of an insertion member 7, a control section 8, a universal cord 9, a connector unit 10, and an electric connector 11. The insertion member 7 is flexible and elongated. The control section 8 is coupled to the proximal end of the insertion member 7. The universal cord 9 that is flexible is extended from the lateral part of the control section 8. The connector unit 10 is fixed to an end of the universal cord 9 and can be attached and detached freely to the light source apparatus 3. The electric connector 11 is jutted out from the lateral part of the connector unit 10 and is freely attached and detached to the signal cable 4. The signal cable 4 that can be coupled to the video processor 5 is plugged in to the electric connector 11 so that it can be unplugged freely.

An anti-insertion member breakage member 12 formed with an elastic member is mounted on a joint between the insertion member 7 and control section 8 in order to prevent abrupt bending of the joint. Likewise, an anti-control section breakage member 13 is mounted on a joint between the control section 8 and universal cord 9. An anti-connector breakage member 14 is mounted on a joint between the universal cord 9 and connector unit 10.

The insertion member 7 consists mainly of a flexible tube 15, a bending section 16, and a distal part 17. The flexible tube 15 is flexible and soft. The bending section 16 located distally to the flexible tube 15 can be bent by manipulating the control section 8. An observation optical system and an illumination optical system that are not shown are incorporated in the distal part 17 located distally to the bending section 16.

The control section 8 has an aeration/perfusion button 21, a suction button 22, an angling knob 23, a plurality of remote-control switches 24, and a therapeutic accessory insertion port 25. The aeration/perfusion button 21 is pressed in order to instruct aeration or perfusion. The suction button 22 is pressed in order to instruct suction. The angling knob 23 is pressed to remotely control the bending section 16. The plurality of remote-control switches 24 is used to remotely control the video processor 5. The therapeutic accessory insertion port 25 is an opening that opens onto a therapeutic accessory channel.

A fluid supply port, an aeration/perfusion nozzle, and a suction port are formed in the distal part 17. When aeration or perfusion is instructed, cleaning fluid or gas is jetted out to an observation window located in front of the observation optical system, which is not shown, through the fluid supply port or an opening of the aeration/perfusion nozzle. The suction port that is not shown is a distal opening of the therapeutic accessory channel that is not shown and that is run through the insertion member 7. A therapeutic accessory is inserted through the suction port, or fluid is sucked from a body cavity through the suction port.

The connector unit 10 has an air supply base 26, a water supply tank pressurization base 28, a fluid supply base 29, a suction base 30, and an injection base 31. The air supply base 26 is connected to an air source, which is not shown, incorporated in the light source apparatus 3 so that it can be disconnected freely. The water supply tank pressurization base 28 and fluid supply base 29 are connected to a water supply tank 27 that is a fluid source so that they can be disconnected freely. The suction base 30 is connected to a sucker, which is not shown, for sucking fluid through the suction port. The injection base 31 is connected to a water supply means, which is not shown, for supplying water through the fluid supply port formed in the distal part 17. Moreover, the connector unit 10 has a ground base 32 through which high-frequency leakage current is fed back to a diathermy device when developed in the endoscope during diathermy.

The electric connector 11 has an air vent hole, which is not shown, linking the interior and exterior of the endoscope 2. A pressure regulating valve-inclusive waterproof cap 33 is freely detachably attached to the electric connector 11. The waterproof cap 33 has a pressure regulating valve that is not shown.

For autoclaving (high-temperature high-pressure steam sterilization), the endoscope 2 is stowed in a sterilization casing 34.

The sterilization casing 34 consists of a tray 35 in which the endoscope 2 is stowed and a lid member 36 that covers the tray 35. The tray 35 and lid member 36 each have a plurality of pores that are not shown. During autoclaving (high-temperature high-pressure steam sterilization), steam permeates through the pores.

The tray 35 has a restriction dent, which is not shown, formed to fit the endoscope 2. The components of the endoscope 2 are settled at predetermined positions in the restriction dent. The restriction dent includes an insertion member restriction dent (not shown) in which the flexible insertion member 7 is settled.

As mentioned above, the typical regulations for high-temperature high-pressure steam sterilization are stipulated in the standard ANSI/AAMI ST 37-1992 approved by the American National Standards Institute (ANSI) and published from the Association for the Advancement of Medical Instrumentation (AAMI). According to the standard, a pre-vacuum sterilization process should be performed at 132° C. for 4 minutes, and a gravity settling sterilization process should be performed at 132° C. for 10 minutes.

The condition of the temperature for high-temperature high-pressure steam sterilization varies depending on the model of a high-temperature high-pressure steam sterilizer or the time required for sterilization. Generally, the temperature ranges from about 115° C. to about 138° C. Some sterilizers can be set to about 142° C. The condition of the time varies depending on the condition of the temperature for sterilization. Generally, the time ranges about 3 minutes to about 60 minutes. Some types of sterilizers can be set to about 100 minutes.

During the sterilization, the pressure in a sterilization chamber is generally higher than the atmospheric pressure by about 0.2 MPa.

A typical pre-vacuum high-temperature high-pressure steam sterilization process includes a pre-vacuum step and a sterilization step. At the pre-vacuum step, the sterilization chamber in which equipment to be sterilized is placed is decompressed in preparation for the sterilization step. At the sterilization step succeeding the pre-vacuum step, high-pressure high-temperature steam is fed into the sterilization chamber in order to sterilize the equipment to be sterilized. The pre-vacuum step is needed to facilitate infiltration of steam into the details of the equipment to be sterilized at the succeeding sterilization step. Decompression of the sterilization chamber allows high-pressure high-temperature steam to spread all over the equipment to be sterilized.

At the pre-vacuum step, the pressure in the sterilization chamber is generally lower than the atmospheric pressure by a value ranging from about 0.07 MPa to about 0.09 MPa.

Some sterilization processes include a dry step at which the sterilization chamber is decompressed again after completion of the sterilization step in order to dry the sterilized equipment to be sterilized. At the dry step, the sterilization chamber is decompressed in order to exhaust steam from the sterilization chamber. This facilitates drying of the equipment to be sterilized in the sterilization chamber. At the dry step, the pressure in the sterilization chamber is generally lower than the atmospheric pressure by a value ranging from about 0.07 MPa to about 0.09 MPa.

For autoclaving the endoscope 2 (sterilizing the endoscope 2 with high-temperature high-pressure steam), the pressure regulating valve-inclusive waterproof cap 33 is attached to the electric connector 11. In this state, the pressure regulating value, which is not shown, of the waterproof cap 33 is closed. The waterproof cap 33 blocks the air vent hole. The interior of the endoscope 2 is sealed to be watertight.

When a sterilization process including the pre-vacuum step is adopted, the pressure in the sterilization chamber is decreased at the pre-vacuum step. When a difference in pressure is created between the interior and exterior of the endoscope 2, that is, the external pressure of the endoscope 2 gets lower than the internal pressure thereof, the pressure regulating valve opens. Consequently, the interior of the endoscope 2 communicates with the exterior thereof through the air vent hole. This prevents creation of a large difference in pressure between the interior of the endoscope 2 and the sterilization chamber. Thus, the endoscope 2 will not be broken due to the difference in pressure between the interior and exterior thereof.

At the sterilization step, the sterilization chamber is pressurized. When a difference in pressure is created between the interior of the endoscope 2 and the exterior thereof, that is, the external pressure of the endoscope 2 gets higher than the internal pressure thereof, the pressure regulating valve is closed. Consequently, high-pressure high-temperature steam will not actively invade into the endoscope 2 through the waterproof cap 33 and air vent hole.

However, high-temperature high-pressure steam gradually invades into the endoscope 2 through the sheathing of the flexible tube and O rings. The sheathing of the flexible tube is made of a high polymer material. The O rings are seal means included in the joints that are integral parts of the housing of the endoscope 2 and made of a fluorocarbon rubber or silicon rubber. Incidentally, pressure that is the sum of pressure released due to decompression performed at the pre-vacuum step and pressure applied at the sterilization step is externally applied to the housing of the endoscope 2.

When a sterilization process including a decompression step preceded by the sterilization step is adopted, the pressure in the sterilization chamber is decreased at the decompression step. Substantially at the same time when a difference in pressure is created between the interior of the endoscope 2 and the exterior thereof, that is, the external pressure of the endoscope 2 gets lower than the internal pressure thereof, the pressure regulating valve opens. The interior of the endoscope 2 communicates with the exterior thereof through the air vent hole. This prevents creation of a large difference in pressure between the interior of the endoscope 2 and the sterilization chamber. Thus, the endoscope 2 will not be broken due to a difference in pressure between the interior and exterior of the endoscope 2.

When the decompression step is completed, the sterilization chamber is pressurized. When a difference in pressure is created between the interior and exterior of the endoscope 2, that is, the external pressure of the endoscope 2 gets higher than the internal pressure thereof, the pressure regulating valve closes.

As mentioned above, when all the steps of a high-temperature high-pressure sterilization process are completed, pressure equivalent to pressure released at the decompression step is externally applied to the housing of the endoscope 2.

When the waterproof cap 33 is detached from the electric connector 11, the interior of the endoscope 2 communicates with the exterior thereof through the air vent hole. This makes the internal pressure of the endoscope 2 equal to the atmospheric pressure. The endoscope 2 is unloaded from the pressure applied to the housing.

As shown in FIG. 2, the flexible tube 15 consists of a spiral tube 37, a braid 38, and a sheathing 39. The spiral tube 37 has a metallic belt wound spirally. The spiral tube 37 is sheathed with the braid 38 woven like a net. The braid 38 is sheathed with the sheathing 39 made of a resin.

The resin made into the sheathing 39 of the flexible tube 15 is selected in consideration of durability for use, performance including inserting smoothness, and chemical resistance against an agent used to clean or disinfect an endoscope. The resin sheathing 39 made of the selected resin dominates the "hardness" of the flexible tube 15. Incidentally, the hardness is numerically expressed in the form of a flexural rigidity calculated as the ratio of force applied to a predetermined length in longitudinal directions of the flexible tube 15 to a predetermined magnitude of bend by which the length is bent. In the present embodiment, the predetermined magnitude of bend is the state of the flexible tube 15 being partly bent to trace a circle of about 20 cm in diameter. The state of the flexible tube 15 being partly bent to trace a circle of about 20 cm in diameter is equivalent to the state of the insertion member being inserted into, for example, the large intestine. Even if efforts are made to insert the insertion member 7 into the large intestine without causing a warp, the insertion member 7 is bent to trace a circle of at least about 20 cm in diameter. The insertion member must therefore be able to be smoothly bent in any situation so that it can be changed from a straight state to the state of being bent to trace a circle of 20 cm in diameter.

In the past, the resin sheathing 39 of the flexible tube 15 is made of a thermosetting resin, for example, a polyimide resin, or a resin such as a urethane resin. The thermosetting resin hardens at the temperature derived from thermal loading caused by high-temperature high-pressure steam sterilization. The softening point of the resin such as a urethane resin is lower than the temperature derived from thermal loading caused by the high-temperature high-pressure steam sterilization. Moreover, the temperature above which the resin such as a urethane resin fails to exert the property thereof with which a feature of an endoscope is guaranteed is lower than the temperature derived from thermal loading caused by the high-temperature high-pressure steam sterilization.

According to the present embodiment, the resin sheathing 39 of the flexible tube 15 is made of, for example, an ester-series thermoplastic elastomer, an amide-series thermoplastic elastomer, or a blend of them so that the sheathing 39 will remain soft even after thermally loaded during high-temperature high-pressure steam sterilization.

Incidentally, the material to be made into the resin sheathing 39 of the flexible tube 15 is not limited to the ester-series thermoplastic elastomer or amide-series thermoplastic elastomer. Alternatively, a styrene resin, an olefine resin, or a blend of them will do.

Next, the braid 38 and spiral tube 37 that are integral parts of the flexible tube 15 will be described in conjunction with FIG. 3A to FIG. 3E.

As shown in FIG. 3A, the spiral tube 37 has a metallic belt wound spirally. The adjoining portions of the wound belt have a certain space x (where x is larger than 0) between each pair of adjoining portions. The space x remains larger than 0 even when the flexible tube 15 contracts because of loading caused by high-temperature high-pressure steam sterilization. Referring to FIG. 3A, the spiral tube 37 has the metallic belt spirally wound by one turn. Depending on a purpose of use or performance, the spiral tube 37 may have the metallic belt spirally wound by two or three turns.

As shown in FIG. 3B and FIG. 3C, for example, when the flexible tube 15 contracts, the space x changes to a space x1 (where x1 is smaller than x) according to the degree of contraction of the flexible tube 15. In this case, when an attempt is made to bend part of the flexible tube 15 by a predetermined magnitude of bend, even if the magnitude of bend is small, the adjoining belt portions of the spiral tube 37 come into contact with one another. This causes repulsion to bending. If the flexible tube 15 contracts, the contraction affects the hardness of the flexible tube 15.

In contrast, when the flexible tube 15 stretches, the space x increases. In this case, when an attempt is made to bend part of the flexible tube 15 by a predetermined magnitude of bend, the adjoining belt portions of the spiral tube 37 will not come into contact with one another. Consequently, the stretch causes the hardness of the flexible tube 15 to get lower, that is, causes the flexible tube 15 to soften.

According to the present embodiment, unless the insertion member 7 is held bent to trace a circle of about 20 cm in diameter after sterilization with high-temperature high-pressure steam, the adjoining belt portions will not come into contact with one another, that is, the space x will not change.

The braid 38 has wires or strands plaited. The strands are plaited to meet at an angle α. The braid 38 is made of SUS, copper, brass, tungsten, iron, or any other metal, or a synthetic resin, a silk yarn, a kite string, or any other nonmetal, or a composite material composed of a plurality of materials selected arbitrarily from among these materials.

As shown in FIG. 3D, the braid 38 has the strands plaited to meet at an angle α. For example, when the flexible tube 15 contracts, if the angle α changes to an angle β (β>α) as shown in FIG. 3E, the braid 38 affects the hardness of the flexible tube 15.

As shown in FIG. 4, metallic angulation wires 41 (angle control wires), tubes or coils (hereinafter angulation coils) 42, a light guide 43, signal cables 44, a therapeutic accessory passage channel 45, and an aeration/perfusion channel 46 are passed through the thus structured flexible tube 15. The angulation wires 41 are used to remotely control the bending section 16. The angulation coils 42 encase the angulation wires 41. Illumination light is propagated over the light guide 43. The signal cables 44 have armors thereof coated with a fluorocarbon resin such as a perfluoroalkoxy resin (PFA). The therapeutic accessory passage channel 45 is made of a fluorocarbon resin such as a polytetrafluoroethylene resin (PTFE). Among the angulation wires 41, angulation coils 42, light guide 43, signal cables 44, therapeutic accessory passage channel 45, and aeration/perfusion channel 46, members that are thermally loaded during high-temperature high-pressure steam sterilization and that affect the hardness of the flexible tube 15 are the light guide 43, signal cables 44, therapeutic accessory passage channel 45, and aeration/perfusion channel 46. These members are made of a combination of materials that, after thermally loaded during sterilization with high-temperature high-pressure steam, exhibit hardnesses equal to or lower than those attained before the materials are thermally loaded during the sterilization. Moreover, a bonding layer 47 for fixing the sheathing 39 to the braid 38 is formed between the sheathing 39 and braid 38. The bonding layer 47 is formed with an adhesive made of an epoxy-series thermoplastic elastomer. Otherwise, the adhesive may not be used but the resin made into the sheathing 39 may be thermally deposited onto the braid 38. Depending on a kind of adhesive, the bonding layer 47 itself may harden. In the present embodiment, the bonding layer 47 is formed with an adhesive that makes the hardness of the flexible tube 15, which is attained after sterilization with high-temperature high-pressure steam, equal to or lower than that attained before the sterilization. hardness of the flexible tube 15.

Thinkable factors causing the hardness of the flexible tube 15 to change will be described below. First, factors causing the flexible tube 15 to harden will be described.

A: Factors Causing the Flexible Tube 15 to Harden (1) The resin made into the sheathing 39 hardens.

(2) When the sheathing 39 contracts, the space x between each pair of the adjoining belt portions of the spiral tube 37 decreases or changes to the space x1 (where x1>0). Consequently, the adjoining belt portions of the spiral tube 37 come into contact with one another before the flexible tube 15 is bent to trace a circle of about 20 cm in diameter.

(3) An adhesive used to form the bonding layer 47 hardens.

(4) Supposing the flexible tube 15 stretches, the angle α at which the strands of the braid 38 meet gets smaller. Namely, the strands of the braid 38 meet at an acute angle in longitudinal directions of the insertion member. Consequently, the resistance exhibited by the strands against bending increases, and the braid 38 hardens.

(5) The sum total of the hardnesses of the built-in components of the flexible tube 15 increases. The built-in components include the angulation wires 41, angulation coils 42, light guide 43, signal cables 44, therapeutic accessory passage channel 45, and aeration/perfusion channel 46.

The factors causing the flexible tube 15 to harden have been described above. Now, factors causing the flexible tube 15 to soften will be described below.

B: Factors Causing the Flexible Tube 15 to Soften (1) The resin made into the sheathing 39 softens.

(2) An adhesive used to form the bonding layer 47 softens.

(3) When the sheathing 39 contracts, the angle α at which the plaited strands of the braid 38 meet changes to the angle β(β>α) as described in conjunction with FIG. 3E. In other words, the plaited strands of the braid 38 come to meet at an obtuse angle in longitudinal directions of the insertion member. Consequently, the resistance exhibited by the strands against bending decreases.

(4) The sum total of the hardnesses of the built-in components, that is, the angulation wires 41, angulation coils 42, light guide 43, signal cables 44, therapeutic accessory passage channel 45, and aeration/perfusion channel 46 decreases.

In the present embodiment, the factors causing the flexible tube 15 to soften are used to balance the factors causing the flexible tube 15 to harden. The hardness of the flexible tube 15 to be attained after sterilization with high-temperature high-pressure steam is thus determined.

As mentioned above, according to the present embodiment, the resin sheathing 39 of the flexible tube 15 is made of an ester-series thermoplastic elastomer or an amide-series thermoplastic elastomer. When the resin such as the ester-series thermoplastic elastomer or amide-series thermoplastic elastomer is heated at least once or a plurality of times, the hardness of the resin attained at the room temperature gets lower. According to the factor B-(1), the hardness of the resin made into the sheathing 39 is lowered. When the sheathing 39 is made of any of the above resins, the hardness of the flexible tube 15 attained after sterilization with high-temperature high-pressure steam is equal to or lower than the hardness attained before the sterilization.

Moreover, the resin sheathing 39 of the flexible tube 15 may be made of an ester-series thermoplastic elastomer as it conventionally is. In this case, the flexible tube 15 may contract in longitudinal directions when thermally loaded during high-temperature high-pressure steam sterilization.

However, according to the present embodiment, even if the flexible tube 15 contracts in longitudinal directions due to thermal loading caused by high-temperature high-pressure steam sterilization, the strands of the braid 38 meet at an obtuse angle in the longitudinal directions of the insertion member. Consequently, the resistance exhibited by the strands against bending decreases. This softens the flexible tube 15. Moreover, according to the present embodiment, the adjoining belt portions of the spiral tube 37 have the space x between each pair of adjoining ones. Unless the flexible tube 15 is held bent to trace a circle of at least 20 cm in diameter after high-temperature high-pressure steam sterilization, the adjoining belt portions will not come into contact with one another, that is, the space x will not change. Therefore, the factor A-(1) will not arise.

Furthermore, according to the present embodiment, the bonding layer 47 is formed between the sheathing 39 and braid 38 in order to fix the sheathing 39 to the braid 38. The bonding layer 47 is formed with an adhesive made of, for example, an epoxy-series thermoplastic elastomer that will not harden at the temperature derived from thermal loading caused by high-temperature high-pressure steam sterilization. The factor A-(3) will therefore not arise. Depending on a kind of adhesive, the bonding strength of the bonding layer 47 may be nullified due to high-temperature high-pressure steam sterilization. The sheathing 39 may therefore be separated from the braid 38. However, when the resin made into the sheathing 39 is thermally deposited on the braid 38, the deposited resin will neither harden nor deteriorate at the temperature derived from thermal loading caused by high-temperature high-pressure steam sterilization. The bonding strength of the deposited resin for bonding the sheathing 39 to the braid 38 remains unchanged.

Moreover, according to the present embodiment, the built-in components of the flexible tube 15 are made of a combination of materials that, after thermally loaded during high-temperature high-pressure steam sterilization, exhibit hardnesses equal to or lower than the hardnesses the materials exhibit before thermally loaded. Herein, the built-in components of the flexible tube 15 are the angulation wires 41, angulation coils 42, light guide 43, signal cables, therapeutic accessory passage channel 45, and aeration/perfusion channel 46. The sum total of the hardnesses of the built-in components decreases. Consequently, the flexible tube 15 can be softened. For example, one of the built-in components may be hardened. Nevertheless, the sum total of the hardnesses of the built-in components, that is, the hardness of the flexible tube 15 attained after the flexible tube 15 is thermally loaded during high-temperature high-pressure steam sterilization should merely be equal to or lower than the hardness thereof attained before the flexible tube is thermally loaded.

Consequently, the hardness of the flexible tube 15 attained after sterilization with high-temperature high-pressure steam is lower than that attained before the sterilization. Once the flexible tube 15 is structured in consideration of the factors A and B, the hardness of the flexible tube 15 attained after sterilization with high-temperature high-pressure steam may be made equal to that attained before the sterilization (the hardness remains unchanged).

Consequently, the hardness of the flexible tube 15 loaded during high-temperature high-pressure steam sterilization is equal to or lower than that of the flexible tube 15 unloaded before the high-temperature high-pressure steam sterilization. Consequently, the flexural rigidity of the flexible tube attained after sterilization with high-temperature high-pressure steam can be made equal to or lower than that attained before the sterilization. The inserting smoothness of the insertion member 7 can be optimized.

The present invention is not limited to the aforesaid embodiment but can be modified or varied within the gist of the present invention.

As described so far, according to the present invention, the flexural rigidity of the flexible tube attained after sterilization with high-temperature high-pressure steam is equal to or lower than that attained before the sterilization. This results in the endoscope having the inserting smoothness of the insertion member optimized.

What is claimed is:

1. An endoscope having an insertion member that includes a flexible tube having a spiral tube formed by spirally winding a metallic belt such that the adjoining portions of the wound belt have a space x between them such that if the flexible tube is held bent by a predetermined magnitude of bend at room temperature, the adjoining portions of the spiral tube of the flexible tube do not come into contact with one another, the insertion member further having a braid for sheathing the spiral tube and a resin sheathing for sheathing the braid, wherein the adjoining portions of the wound belt have a space X1 between them even if the flexible tube contracts in longitudinal directions after being subjected to high-temperature high-pressure steam sterilization, and the space X1 allows the flexible tube to be bent to trace a circle of at least about 20 cm in diameter at the room temperature, wherein the adjoining portions of the spiral tube of the flexible tube do not come into contact with one another.

2. An endoscope according to claim 1, wherein the high-temperature high-pressure steam sterilization is achieved at a loading step at a temperature ranging from substantially 115° C. to substantially 140° C.

3. An endoscope according to claim 1, wherein the resin sheathing of the flexible tube is made of a resin of either an ester-series thermoplastic elastomer or an amide-series thermoplastic elastomer.

4. An endoscope having an insertion member that includes a flexible tube having a spiral tube formed by spirally winding a metallic belt, the insertion member further having a braid for sheathing the spiral tube and a resin sheathing for sheathing the braid and also having a bonding layer between the sheathing and the braid for fixing the sheathing to the braid, the insertion member further includes a plurality of built-in components at least one of which is a light guide, the endoscope provided with either of the following a) and b):
   a) wherein the bonding layer is made of an epoxy-series thermoplastic elastomer; and
   b) wherein the sum total of hardness of the built-in components attained at room temperature after being loaded during high-temperature high-pressure steam sterilization becomes lower than that attained before being loaded.

5. An endoscope according to claim 4, wherein the high-temperature high-pressure steam sterilization is achieved at a loading step at a temperature ranging from substantially 115° C. to substantially 140° C.

6. An endoscope according to claim 4, wherein the resin sheathing of the flexible tube is made of a resin of either an ester-series thermoplastic elastomer or an amide-series thermoplastic elastomer.

7. An endoscope having an insertion member that includes a flexible tube having a spiral tube formed by spirally winding a metallic belt such that adjoining portions of the wound belt have a space x between them and such that the flexible tube is held bent by a predetermined magnitude of bend at room temperature, the adjoining portions of the spiral tube of the flexible tube do not come into contact with one another, the insertion member further having a braid for sheathing the spiral tube, and a resin sheathing for sheathing the braid, and also having a bonding layer between the sheathing and the braid for fixing the sheathing to the braid, the insertion member further includes a plurality of built-in components at least one of which is a light guide, the endoscope provided with one of the following a), b) and c):
   a) wherein the adjoining portions of the wound belt have a space X1 between them even if the flexible tube contracts in longitudinal directions after being subjected to high-temperature high-pressure steam sterilization, and the space X1 allows the flexible tube to be bent to trace a circle of at least about 20 cm in diameter at the room temperature, wherein the adjoining portions of the spiral tube of the flexible tube do not come into contact with one another;
   b) wherein the bonding layer is made of an epoxy-series thermoplastic elastomer; and
   c) wherein the sum total of hardness of the built-in components attained at room temperature after being loaded during high-temperature high-pressure steam sterilization becomes lower than that attained before being loaded.

8. An endoscope according to claim 7, wherein the high-temperature high-pressure steam sterilization is achieved at a loading step at a temperature ranging from substantially 115° C. to substantially 140° C.

9. An endoscope according to claim 7, wherein the resin sheathing of the flexible tube is made of a resin of either an ester-series thermoplastic elastomer or an amide-series thermoplastic elastomer.

10. An endoscope having an insertion member that includes a flexible tube having a spiral tube formed by spirally winding a metallic belt such that the adjoining portions of the wound belt have a space x between them and such that if the flexible tube is held bent by a predetermined magnitude of bend at room temperature, the adjoining portions of the spiral tube of the flexible tube do not come into contact with one another, the insertion member further having a braid for sheathing the spiral tube and a resin sheathing for sheathing the braid, and also having a bonding layer between the sheathing and the braid for fixing the sheathing to the braid, the insertion member further includes a plurality of built-in components at least one of which is a light guide, the endoscope provided with at least two of the following a), b), and c):
   a) wherein the adjoining portions of the wound belt have a space X1 between them even if the flexible tube contracts in longitudinal directions after being subjected to high-temperature high-pressure steam sterilization, and the space X1 allows the flexible tube to be bent to trace a circle of at least about 20 cm in diameter at the room temperature, wherein the adjoining portions of the spiral tube of the flexible tube do not come into contact with one another;
   b) wherein the bonding layer is made of an epoxy-series thermoplastic elastomer; and
   c) wherein the sum total of hardness of the built-in components attained at room temperature after being loaded during high-temperature high-pressure steam sterilization becomes lower than that attained before being loaded.

11. An endoscope according to claim 10, wherein the high-temperature high-pressure steam sterilization is achieved at a loading step at a temperature ranging from substantially 115° C. to substantially 115° C.

12. An endoscope according to claim 10, wherein the resin sheathing of the flexible tube is made of a resin of either an ester-series thermoplastic elastomer or an amide-series thermoplastic elastomer.

13. An endoscope having an insertion member that includes a flexible tube having a spiral tube formed by spirally winding a metallic belt, the insertion member further having a braid for sheathing the spiral tube and a resin sheathing for sheathing the braid and also having a bonding layer for fixing the sheathing to the braid between the sheathing and the braid, the endoscope provided with:
   a) the bonding layer being made of an epoxy-series thermoplastic elastomer; and
   b) the sum total of hardness of at least a light guide built-in component attained at room temperature after being loaded during high-temperature high-pressure steam sterilization becomes equal to that attained before being loaded.

14. An endoscope according to claim 13, herein the high-temperature high-pressure steam sterilization is achieved at a loading step at a temperature ranging from substantially 115° C. to substantially 140° C.

15. An endoscope according to claim 13, wherein the resin sheathing of the flexible tube is made of a resin of either an ester-series thermoplastic elastomer or an amide-series thermoplastic elastomer.

16. An endoscope having an insertion member that includes a flexible tube having a spiral tube formed by spirally winding a metallic belt such that the adjoining portions of the wound belt have a space x between them and such that if the flexible tube is held bent by a predetermined magnitude of bend at room temperature, the adjoining portions of the spiral tube of the flexible tube do not come into contact with one another, the insertion member further having a braid for sheathing the spiral tube, and a resin sheathing for sheathing the braid, and also having a bonding layer for fixing the sheathing to the braid between the sheathing and the braid, the endoscope provided with at least two of the following a), b) and c):
   a) the adjoining portions of the wound belt having a space X1 between them even if the flexible tube contracts in longitudinal directions after being subjected to high-temperature high-pressure steam sterilization, and the space X1 allows the flexible tube to be bent to trace a circle of at least about 20 cm in diameter at the room temperature, wherein the adjoining portions of the spiral tube of the flexible tube do not come into contact with one another;
   b) the bonding layer being made of an epoxy-series thermoplastic elastomer; and
   c) the sum total of hardness of at least a light guide built-in component attained at room temperature after being loaded during high-temperature high-pressure steam sterilization becomes equal to that attained before being loaded.

17. An endoscope claim 16, wherein the high-temperature high-pressure steam sterilization is achieved at a loading step at a temperature ranging from substantially 115° C. to substantially 140° C.

18. An endoscope according to claim 16, wherein the resin sheathing of the flexible tube is made of a resin of either an ester-series thermoplastic elastomer or an amide-series thermoplastic elastomer.

19. An endoscope having an insertion member that includes a flexible tube having a spiral tube formed by spirally winding a metallic belt such that the adjoining portions of the wound belt have a space x between them such that if the flexible tube is held bent by a predetermined magnitude of bend at room temperature, the adjoining portions of the spiral tube of the flexible tube do not come into contact with one another, the insertion member further having a braid for sheathing the spiral tube and a resin sheathing for sheathing the braid, and also having a bonding layer for fixing the sheathing to the braid between the sheathing and the braid, the endoscope provided with at least two of the following a), b) and c):
   a) the adjoining portions of the wound belt have a space X1 between them even if the flexible tube contracts in longitudinal directions after being subjected to high-temperature high-pressure steam sterilization, and the space X1 allows the flexible tube to be bent to trace a circle of at least about 20 cm in diameter at the room temperature, wherein the adjoining portions of the spiral tube of the flexible tube do not come into contact with one another;
   b) the bonding layer being made of an epoxy-series thermoplastic elastomer; and
   c) the sum total of hardness of at least a built-in component attained at room temperature after being loaded during high-temperature high-pressure steam sterilization becomes equal to that attained before being loaded.

20. An endoscope according to claim 19, wherein the high-temperature high-pressure steam sterilization is achieved at a loading step at a temperature ranging from substantially 115° C. to substantially 140° C.

21. An endoscope according to claim 19, wherein the resin sheathing of the flexible tube is made of a resin of either an ester-series thermoplastic elastomer or an amide-series thermoplastic elastomer.

* * * * *